US011504693B2

(12) United States Patent
Barthelet et al.

(10) Patent No.: US 11,504,693 B2
(45) Date of Patent: Nov. 22, 2022

(54) ALUMINA-BASED ADSORBENT CONTAINING SODIUM AND DOPED WITH AN ALKALI ELEMENT FOR CAPTURING ACIDIC MOLECULES

(71) Applicant: IFP Energies nouvelles, Rueil-Malmaison (FR)

(72) Inventors: Karin Barthelet, Lyons (FR); Arnaud Baudot, Vernaison (FR); Marc-Antoine Lelias, Ales (FR); Olivier Ducreux, Louveciennes (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 455 days.

(21) Appl. No.: 15/500,843

(22) PCT Filed: Jun. 22, 2015

(86) PCT No.: PCT/EP2015/063994
§ 371 (c)(1),
(2) Date: Jan. 31, 2017

(87) PCT Pub. No.: WO2016/015923
PCT Pub. Date: Feb. 4, 2016

(65) Prior Publication Data
US 2017/0225144 A1  Aug. 10, 2017

(30) Foreign Application Priority Data
Jul. 31, 2014  (FR) ...................................... 14/57406

(51) Int. Cl.
*B01J 20/08* (2006.01)
*B01J 20/04* (2006.01)
*B01D 53/02* (2006.01)
*B01J 20/28* (2006.01)
*B01J 20/30* (2006.01)
*B01J 20/32* (2006.01)
*B01J 20/34* (2006.01)
*C07C 7/12* (2006.01)

(52) U.S. Cl.
CPC ............ *B01J 20/041* (2013.01); *B01D 53/02* (2013.01); *B01J 20/08* (2013.01); *B01J 20/28059* (2013.01); *B01J 20/28061* (2013.01); *B01J 20/28069* (2013.01); *B01J 20/28071* (2013.01); *B01J 20/28073* (2013.01); *B01J 20/3007* (2013.01); *B01J 20/3021* (2013.01); *B01J 20/3078* (2013.01); *B01J 20/3204* (2013.01); *B01J 20/3236* (2013.01); *B01J 20/3433* (2013.01); *B01J 20/3483* (2013.01); *B01J 20/3491* (2013.01); *C07C 7/12* (2013.01); *B01D 2251/304* (2013.01); *B01D 2251/306* (2013.01); *B01D 2253/104* (2013.01); *B01D 2253/25* (2013.01); *B01D 2253/304* (2013.01); *B01D 2253/306* (2013.01); *B01D 2253/311* (2013.01); *B01D 2256/24* (2013.01); *B01D 2257/308* (2013.01); *B01D 2257/504* (2013.01); *B01D 2259/402* (2013.01); *B01D 2259/4009* (2013.01); *Y02C 20/40* (2020.08)

(58) Field of Classification Search
None
See application file for complete search history.

(56) References Cited

U.S. PATENT DOCUMENTS

| 4,364,858 | A | 12/1982 | Goodboy |
| 4,835,338 | A | 5/1989 | Liu |
| 5,316,998 | A | 5/1994 | Lee et al. |
| 5,505,926 | A | 4/1996 | Lee et al. |
| 5,595,954 | A | 1/1997 | Lee et al. |
| 6,125,655 | A | 10/2000 | Millet et al. |
| 9,486,738 | B2 | 11/2016 | Porcheron et al. |
| 2013/0341564 | A1 | 12/2013 | Porcheron et al. |

FOREIGN PATENT DOCUMENTS

| EP | 3922482 A1 | 6/1999 |
| FR | 2486822 A1 | 1/1982 |
| FR | 2690855 A1 | 11/1993 |
| FR | 2992233 A1 | 12/2013 |

OTHER PUBLICATIONS

International Search Report for PCT/EP2015/063994 dated Sep. 28, 2015.
Euzen, P. et al., "'Alumina' In; 'Handbook of Porous solids'" Apr. 25, 2008, pp. 1591-1677.

*Primary Examiner* — Tam M Nguyen
(74) *Attorney, Agent, or Firm* — Millen, White, Zelano and Branigan, P.C.; Harry B. Shubin

(57) ABSTRACT

The present invention relates to an adsorbent comprising an alumina support and at least one alkali element, said adsorbent being obtained by introducing at least one alkali element, identical to or different from sodium, onto an alumina support the sodium content of which, expressed as $Na_2O$ equivalent, before the introduction of the alkali element or elements, is comprised between 1000 and 5000 ppm by weight with respect to the total weight of the support. The invention also relates to processes for the preparation of said adsorbent and use thereof in a process for the elimination of acidic molecules such as COS and/or $CO_2$.

6 Claims, No Drawings

ALUMINA-BASED ADSORBENT CONTAINING SODIUM AND DOPED WITH AN ALKALI ELEMENT FOR CAPTURING ACIDIC MOLECULES

The present invention relates to an alumina-based adsorbent for the elimination of acidic molecules such as COS and/or $CO_2$ contained in liquid or gaseous hydrocarbon flows. The invention also relates to processes for the preparation of this adsorbent as well as use thereof in a process for the elimination of acidic molecules from a flow of liquid or gaseous hydrocarbons.

State of the Art

Acidic molecules such as carbonyl sulphide (COS), carbon dioxide ($CO_2$), hydrogen sulphide ($H_2S$) or also carbon disulphide ($CS_2$) are contaminants that are present in natural gas, the various synthesis gases and combustion gases and the liquid hydrocarbon cuts originating from petroleum or from the transformation of biomass.

Now, these acidic molecules are harmful from several standpoints. From an environmental standpoint, it is well known that $CO_2$ for example is one of the gases responsible for the greenhouse effect. COS, in its turn, once it has been released into the atmosphere via the gaseous effluents from refining and petrochemical processes, can be carried into the stratosphere, where it will alter the ozone concentration via its effect of promoting photochemical reactions and will lead to the formation of $SO_2$. It will therefore simultaneously contribute to global warming and intensify acid rain. From an industrial standpoint, the acidic molecules accentuate the phenomena of corrosion of reactors for refining and for the petrochemical industry. Moreover, they contribute to the presence of sulphur in gas and oil products and can therefore cause them to fail to comply with specifications. Finally, they are poisons for many catalysts and in particular those for the polymerization of olefins.

It is therefore sought to eliminate the acidic molecules, in particular COS and $CO_2$, contained in the various hydrocarbon flows.

COS present in liquid hydrocarbons and in particular in olefins can be eliminated in various ways.

The first method is to treat the effluent containing COS with physical solvents (for example soda) or with chemical solvents (such as amines), i.e. to transpose the methods of absorption from $CO_2$ to COS, as the two molecules have similar properties, including an acidic character. The use of soda makes it possible, as expected, to absorb COS, but at rates 1000 times slower than in the case of $CO_2$ (Scott Elliott, Eric Read, Sherwood Rowland, Rates of mechanisms for the hydrolysis of COS in natural waters, Environ. Sci. Technol., 1989, 23 (4), 458-461). The same problem of much slower reaction with COS than with $CO_2$ is encountered if COS is to be reacted with primary or secondary amines (Sharma M. M. Kinetics of Reactions of Carbonyl Sulphide and Carbon Dioxide with Amines and Catalysis by Brensted Bases of the Hydrolysis of COS. Trans. Faraday Soc., 1965, 61, 681). Moreover, COS tends to react irreversibly with amines, leading to their degradation (Bacon T. R., Pearce R. L., Foster W. R., $H_2S$ selectivity with carbonyl sulphide removal to less than ppm levels, 1986, Presented at the National Petroleum Refiners Association, 23-25 March, Los Angeles). Finally, the reactivity of COS with tertiary amines is very low (Littel R. J., Versteeg G. F., Swaaij W. P. M. Kinetic study of COS with tertiary alkanolamine solutions. Experiments in an intensively Stirred Batch reactor, Ind. Eng. Chem. Res., 1992, 31, 1262-1269). Basically, this process of eliminating COS is not very effective and would be expensive to implement.

The second method often mentioned in the literature is the hydrolysis of COS according to the reaction: $COS+H_2O \rightarrow CO_2+H_2S$. This reaction is thermodynamically favourable, all the more so at low temperature and with a high concentration of COS. However, it is kinetically slow and the conversion rates may not reach 100%, in particular at low temperature. According to U.S. Pat. No. 4,491,516, this problem can be solved by adding water to the alumina. Besides the fact that at low temperature, water becomes a competitor of COS, the main drawback of this process is still that all it does is to transform COS into another sulphur-containing compound, which in its turn will have to be eliminated from the effluent.

Finally, the third method is the adsorption of COS on a basic solid. Most often this uses porous supports impregnated with one or more so-called active phases, but the supports can be used alone. Any conventional porous solids have been mentioned as the support: oxides, mainly alumina, activated carbons, silica-aluminas, clays, zeolites (Y, X, A, BEA), as they are or exchanged with cations such as Ag, Cu, Zn, Fe, Co, Ni, and basic resins. Nearly all the elements can be used as the active phase: alkalis, alkaline-earths (in the form of oxides or sulphates), transition metals (essentially those of the first series, but Pt in the sulphide form, Co and Mo are also mentioned) and the rare earths. However, not all of them have the qualities required for the purification of liquid hydrocarbons containing COS, namely a high adsorption capacity and a good regenerability. For the basic anion-exchange resins (BE 685521 and U.S. Pat. No. 3,282,831), the problem is a residual COS content of the order of ppm, which is still too high (EP 0 169 828). In the case of zeolites and the purification of olefins, the main problem is the degradation of the adsorbent via the formation of coke (S. Watson, R. Kummitt, R. B. Rhinesmith, *Oil & Gas Journal*, 2003, 101, pp 66-73).

The most suitable solids are the oxides and more particularly alumina, especially for low-temperature adsorption. Document U.S. Pat. No. 4,835,338 proposes an activated alumina impregnated with one or more alkali and/or alkaline-earth metals at a level from 0.01 to 10% by weight of metal for the elimination of COS from a liquid propylene feedstock. Once saturated, the adsorbent is regenerated by passing a hot gas (100-300° C.) through it. However, the performance of the solid declines with regenerations (loss of 70% of the initial capacity in the 4th cycle for the solid with the best performance given in the examples). In order to overcome this problem while maintaining a conventional regeneration temperature, i.e. between 100 and 350° C., document U.S. Pat. No. 6,843,907 suggests a two-step regeneration: passage of a hot gas (hydrocarbons, nitrogen or inert gas) containing a hydrolysing agent such as water between 20 and 6000 ppm and then passage of a hot gas without this same agent. The stability of the initial performance of the aluminas tested is maintained for 12 cycles. However, carrying out a regeneration procedure of this kind complicates the implementation of the process. It would therefore be useful to find an adsorbent with adsorption capacities that are equally as good and moreover are stable during the adsorption/desorption cycles without having to add an agent to the regenerating gas.

As for $CO_2$, it is a poison for polymerization catalysts and must therefore be eliminated from the olefinic cuts and more particularly from the ethylene or propylene cuts regardless of their origin. They can in particular originate from thermal or catalytic cracking, but also from the conversion of alcohols to olefins. $CO_2$ can be eliminated by i) absorption with physical or chemical solvents, ii) use of membranes or iii) adsorption on adsorbents. The first two solutions are not suitable for the feedstocks envisaged, which contain very little $CO_2$ (less than 1000 ppmv) and/or are expensive to implement in order to achieve the required specifications (less than 1 ppmv). Therefore the solution adopted is often the use of a solid adsorbent.

Certain patents claim the use of zeolites such as zeolite A (GB 898,321), 13X (EP 0 173 501) or also clinoptilolite (U.S. Pat. No. 4,935,580). Although all of these zeolites have adsorption selectivity in favour of $CO_2$, their capacity for $CO_2$ at a content below 1000 ppmv in an olefinic cut is very low. Moreover, they have the drawback that they need preloading to avoid being heated and degraded. Finally, they often deactivate rapidly during the cycles as a result of the formation and then the deposition of coke on their surface.

Other patents instead propose the use of alkali carbonates alone (U.S. Pat. No. 1,831,731) or in a mixture with alumina (U.S. Pat. Nos. 3,511,595, 3,865,924, US 2007/0037702). However, their optimum reactivity requires the presence of water, so that the following reaction can take place: $MCO_3 + H_2O + CO_2 \rightleftharpoons 2MHCO_3$, where M is an alkali cation. Aluminas promoted with alkali metals and/or alkaline-earth metals are also claimed (U.S. Pat. Nos. 4,433,981, 6,125,655). In fact, document U.S. Pat. No. 4,433,981 proposes an alumina impregnated with one or more alkali metals and/or alkaline-earth metals for the elimination of $CO_2$ from a liquid propylene feedstock. It describes that the impurities contained in the alumina do not affect the performance of the adsorbent. This document in particular describes an alumina having a sodium content of 4700 ppm by weight (equivalent to a content of 6300 ppm by weight expressed as $Na_2O$) impregnated with one or more alkali metals and/or alkaline-earth metals. The adsorbents described in this document are prepared by calcination at relatively high temperature, leading to the formation of aluminates of alkali metals or aluminates of alkaline-earth metals.

SUMMARY OF THE INVENTION

The present invention relates to an alumina-based adsorbent doped with an alkali element for the elimination of acidic molecules such as COS and/or $CO_2$ contained in liquid or gaseous hydrocarbon flows.

More particularly, the present invention relates to an adsorbent comprising an alumina support and at least one alkali element, said adsorbent being obtained by introducing at least one alkali element, identical to or different from sodium, onto an alumina support the sodium content of which, expressed as $Na_2O$ equivalent, before the introduction of the alkali element or elements, is comprised between 1000 and 5000 ppm by weight with respect to the total weight of the support.

Surprisingly, the applicant discovered that the presence of a certain low sodium content in an alumina before it is doped later with at least one alkali element made it possible to obtain an adsorbent having high capacities for the adsorption of acidic molecules, and in particular of COS and/or $CO_2$, and which in particular has stable performance during cycles of adsorption/regeneration without implementing special conditions for regeneration. Without being bound to any theory, the presence of a certain quantity of sodium in the alumina before the introduction of the alkali element or elements would allow filling of the surface defects of the alumina and prevent the formation of elemental sulphur in the case of adsorption of COS, observed on the solids prepared on alumina supports that have not been stabilized with sodium, and which causes deactivation of the adsorbent over time. However, too much sodium on the surface of the support could reduce the interaction between said support and the phase to be introduced (alkali element): the rather basic precursor will be less attracted by the surface if the latter has previously been made too basic. This could lead to poorer dispersion of the active phase and therefore adversely affect the efficacy of the adsorbent in its subsequent use. The final adsorbent having an alkaline-based active phase bound less strongly to the surface of its support could also be prone to releasing a proportion of its active phase, in particular when it is used in the liquid phase. The presence of an optimum quantity of sodium in the alumina, combined with the introduction of the alkali element or elements, thus creates a synergistic effect, which is reflected in a high adsorption capacity and a performance that is more stable over time during the cycles of adsorption/regeneration.

Moreover, the regeneration of the adsorbent according to the invention can be carried out without the need to add a hydrolysis agent to the regenerating gas.

According to a variant, the alkali element is selected from sodium and potassium.

According to a variant, the content of alkali element with respect to the total weight of the adsorbent is comprised between 1 and 60% by weight of said element.

According to a variant, the sodium content, expressed as $Na_2O$ equivalent, in the alumina support before the introduction of the alkali element or elements is comprised between 1500 and 3500 ppm by weight with respect to the total weight of the support.

According to a variant, before the introduction of the alkali element or elements the alumina support has a total pore volume comprised between 0.3 and 1 $cm^3.g^{-1}$ and a specific surface area comprised between 50 and 450 $m^2.g^{-1}$.

According to a variant, the adsorbent according to the invention is constituted by potassium and an alumina support having a sodium content, expressed as $Na_2O$ equivalent, before the introduction of potassium comprised between 1500 and 3500 ppm by weight with respect to the total weight of the support.

The invention also relates to a process for the preparation of the adsorbent according to the invention, comprising the following steps:

a) preparing an aqueous solution containing at least one alkali precursor, b) impregnating an alumina support having a sodium content, expressed as $Na_2O$ equivalent, comprised between 1000 and 5000 ppm by weight with respect to the total weight of the support, with the aqueous solution obtained at the end of step a), c) leaving the impregnated support originating from step b) to mature in a water-saturated closed vessel, d) drying the solid originating from step c).

According to another variant, the process for the preparation of the adsorbent comprises the following steps:

a') mixing an alumina support having a sodium content, expressed as $Na_2O$ equivalent, comprised between 1000 and 5000 ppm by weight with respect to the total weight of the support, with a powder of at least one alkali precursor, b') optionally grinding the mixture obtained at the end of step a') to a granulometry comprised between 2 and 100 µm, c') forming the mixture originating from step b') in the presence of water so as to obtain a material, d') drying the formed material originating from step c').

According to another variant, the process for the preparation of the adsorbent comprises the following steps:
- a") mixing an alumina support having a sodium content, expressed as $Na_2O$ equivalent, comprised between 1000 and 5000 ppm by weight with respect to the total weight of the support, with a solution comprising at least one alkali precursor, in order to obtain a paste,
- b") forming the paste obtained in step a"),
- c") drying the formed paste originating from step b").

According to a variant, a step of calcination under air in a dry or humid atmosphere is carried out at the end of the drying step in the three processes of preparation.

The invention also relates to a process for the elimination of an acidic molecule from a hydrocarbon flow containing at least one acidic molecule, in which the hydrocarbon flow is brought into contact, during an adsorption step, with an adsorbent according to the invention or prepared by one of the processes of preparation according to the invention.

According to a preferred variant, the acidic molecule to be eliminated is COS and/or $CO_2$.

According to a variant, the adsorption step is implemented at a temperature between −50 and 100° C., at an absolute pressure comprised between 0.01 MPa and 5 MPa, and at an hourly space velocity comprised between 50 and 50000 $h^{-1}$.

According to a variant, a step of regeneration of the adsorbent is carried out once the adsorbent is at least partially saturated with acidic molecules.

According to a variant, the regeneration step is carried out by bringing the adsorbent, at least partially saturated with acidic molecules, into contact with a gas or a liquid at a temperature comprised between 20 and 500° C., at an absolute pressure comprised between 0.01 MPa and 5 MPa and at an hourly space velocity comprised between 50 and 50000 $h^{-1}$.

DETAILED DESCRIPTION OF THE INVENTION

The present invention relates to an adsorbent comprising an alumina support and at least one alkali element, said adsorbent being obtained by introducing at least one alkali element, identical to or different from sodium, onto an alumina support the sodium content of which, expressed as $Na_2O$ equivalent, before the introduction of the alkali element or elements, is comprised between 1000 and 5000 ppm by weight with respect to the total weight of the support.

The adsorbent according to the invention comprises at least one alkali element, identical to or different from sodium, introduced onto the alumina, which itself has a certain sodium content. The alkali element introduced is selected from the elements of group IA because of their ability to make the alumina support more basic. Preferably, the alkali element is selected from sodium (Na) and potassium (K). Particularly preferably, the alkali element is potassium. In fact, the applicant has noted that the performance of the adsorbent is improved even more when potassium is used as the alkali element.

Preferably, the content of alkali element with respect to the total weight of the adsorbent is comprised between 1 and 60% by weight of said element, preferably comprised between 2 and 40% by weight, and very preferably comprised between 2 and 20% by weight, or even between 2 and 15% by weight or between 4 and 15% by weight. The content of alkali element is measured by atomic absorption spectrometry, a process described in "Physicochemical analysis of industrial catalysts-Practical manual for characterization" written under the coordination of John Lynch, Editions Technip 2001, pages 31-46.

The adsorbent according to the invention also comprises an alumina support having a sodium content, expressed as $Na_2O$ equivalent, comprised between 1000 and 5000 ppm by weight before the introduction of the alkali element or elements with respect to the total weight of the support. The characteristics of the alumina support containing sodium, mentioned in the present description, correspond to the characteristics of the support before the alkali element or elements were introduced onto the support.

The sodium content, expressed as $Na_2O$ equivalent, of said alumina support before the introduction of the alkali element or elements is comprised between 1000 and 5000 ppm by weight with respect to the total weight of the support. Preferably, the sodium content, expressed as $Na_2O$ equivalent, of said alumina support before the introduction of the alkali element or elements is comprised between 1250 and 4000 ppm, and particularly preferably comprised between 1500 and 3500 ppm. The content of alkali element is measured by atomic absorption spectrometry, a process described in the work cited above.

Without wishing to be bound to any theory, the presence of a certain sodium content in the alumina before the introduction of the alkali element or elements would allow filling of the surface defects of the alumina and prevent the formation of elemental sulphur in the case of adsorption of acidic molecules containing sulphur, which is the source of deactivation of the sites for adsorption of acid gases on the surface of the adsorbent.

An insufficient sodium content in the alumina before the introduction of the alkali element or elements, i.e. a content below 1000 ppm with respect to the total weight of the support, does not make it possible to observe the increase in adsorption capacity and performance that is more stable over time during the cycles of adsorption/regeneration. An insufficient content does not therefore seem to allow filling of the surface defects of the alumina.

Similarly, an excessive content of sodium in the alumina before the introduction of the alkali element or elements, i.e. a content, expressed as $Na_2O$ equivalent, greater than 5000 ppm by weight with respect to the total weight of the support, does not make it possible to observe the increase in adsorption capacity and performance that is more stable over time during the cycles of adsorption/regeneration.

The alumina support advantageously has a total pore volume comprised between 0.3 and 1 $cm^3.g^{-1}$, preferably between 0.4 and 0.7 $cm^3.g^{-1}$. The total pore volume is measured by mercury porosimetry according to standard ASTM D4284 with a wetting angle of 140°, as described in the work Rouquerol F.; Rouquerol J.; Singh K. "Adsorption by Powders & Porous Solids: Principle, methodology and applications", Academic Press, 1999, for example by means of the model Autopore III™ trade mark Micromeritics™.

The specific surface area of the alumina support is advantageously comprised between 50 and 450 $m^2.g^{-1}$, preferably between 100 and 400 $m^2.g^{-1}$, more preferably between 150 and 370 $m^2.g^{-1}$, even more preferably between 200 and 350 $m^2.g^{-1}$. The specific surface area is determined in the present invention by the B.E.T method according to standard ASTM D3663, a method that is described in the same work cited above.

Preferably, said alumina support has a crystallographic structure of the transition alumina type such as a chi, gamma, delta, theta, rho or eta alumina, alone or in a mixture. More preferably, the alumina is a chi, gamma or delta transition alumina, alone or in a mixture. The crystallographic phases are generally obtained from diffraction patterns obtained by X-ray diffraction.

Preferably, the adsorbent according to the invention is constituted by at least one alkali element and an alumina support having a sodium content, expressed as $Na_2O$ equivalent, before the introduction of the alkali element or elements, comprised between 1000 and 5000 ppm by weight with respect to the total weight of the support. Particularly preferably, the adsorbent according to the invention is constituted by potassium and an alumina support having a sodium content, expressed as $Na_2O$ equivalent, before the introduction of the alkali element or elements, comprised between 1000 and 5000 ppm by weight with respect to the total weight of the support. Even more preferably, the adsorbent according to the invention is constituted by potassium and an alumina support having a sodium content, expressed as $Na_2O$ equivalent, before the introduction of the alkali element or elements, comprised between 1500 and 3500 ppm by weight with respect to the total weight of the support.

The alumina support, having a sodium content, expressed as $Na_2O$ equivalent, before the introduction of the alkali element or elements, comprised between 1000 and 5000 ppm by weight with respect to the total weight of the support, can be synthesized by various processes known to a person skilled in the art, for example by the processes described below.

According to the first method of synthesis of the support, rapid dehydration of a precursor of the aluminium trihydroxide type $(Al(OH)_3)$ (otherwise called hydrargillite or gibbsite) for example originating from the process that is commonly called the "Bayer" process, is carried out. Then forming is carried out, for example by granulation, then a hydrothermal treatment and finally calcination, which leads to the production of alumina. This method is in particular described in detail in the document P. Euzen, P. Raybaud, X. Krokidis, H. Toulhoat, J. L. Le Loarer, J. P. Jolivet, C. Froidefond, Alumina, in Handbook of Porous Solids, Editors F. Schüth, K. S. W. Sing, J. Weitkamp, Wiley-VCH, Weinheim, Germany, 2002, pp. 1591-1677. This method makes it possible to produce an alumina that is commonly called "flash alumina".

According to the second method of synthesis of the support, a process is implemented for obtaining gel constituted by a precursor of the gamma-aluminium oxy(hydroxide) (AlO(OH) type—otherwise called boehmite—having high values of specific surface areas comprised between 150 and 600 m²/g. Then the gel is formed, for example by mixing-extrusion. Then a series of thermal or hydrothermal treatments is carried out on the product, leading to the production of alumina. Boehmite gel can be obtained for example by precipitation of basic and/or acid solutions of aluminium salts induced by a change in pH or any other process known to a person skilled in the art. This process is in particular described in the same work cited above. This process makes it possible to produce an alumina that is commonly called "alumina gel".

The sodium present in the alumina support is generally introduced during or after synthesis of the alumina, but always before the introduction of the alkali element or elements. More particularly, the sodium present in the support can already be present in the alumina precursors of the two processes for the preparation of alumina described above, i.e. in the precursor of the aluminium trihydroxide type $(Al(OH)_3)$ or in the precursor of the gamma-aluminium oxy(hydroxide) type (AlO(OH)). The sodium present in the alumina support can also be introduced in the desired quantity into the support either during forming of the support, for example during the granulation step in the synthesis of a flash alumina or in the step of mixing-extrusion in the synthesis of an alumina gel, or also by impregnation of the alumina precursor.

Preferably, the first process of synthesis of the alumina support of the adsorbent according to the invention is implemented. It is in fact known that an alumina prepared by rapid dehydration of a precursor of the trihydroxide type (flash alumina) as a general rule has a higher sodium content than an alumina prepared from an alumina gel.

The alumina support, and therefore the adsorbent according to the invention, can be in the form of a plurality of elements, each element having the form of a bead, cylinder, multilobed extrudate (for example trilobed or quadrilobed), cartwheel, hollow cylinder or any other geometric shape used by a person skilled in the art. Each of the elements constituting the adsorbent complies with the characteristics of the adsorbent according to the invention. More preferably, the alumina support, and therefore the adsorbent according to the invention, is in the form of a plurality of beads with diameters comprised between 0.4 and 100 mm, preferably comprised between 0.5 and 50 mm, more preferably comprised between 0.5 and 10 mm.

Process for the Preparation of the Adsorbent

The invention also relates to processes for the preparation of the adsorbent according to the invention. The adsorbent according to the invention can be prepared by depositing the alkali element on the porous support described above, by synthesis routes known to a person skilled in the art, for example by dry or wet impregnation, by co-granulation, or by co-mixing.

According to a first variant, the process for the preparation of the adsorbent according to the invention comprises the following steps:
 a) preparing an aqueous solution containing at least one alkali precursor,
 b) impregnating an alumina support having a sodium content, expressed as $Na_2O$ equivalent, comprised between 1000 and 5000 ppm by weight with respect to the total weight of the support, with the aqueous solution obtained at the end of step a),
 c) leaving the impregnated support originating from step b) to mature in a water-saturated closed vessel,
 d) drying the solid originating from step c).

According to a variant of the process, drying can be followed by a step e) of calcination in dry or humid air.

According to step a) of the first variant of the process of preparation, an aqueous solution is prepared containing at least one alkali precursor.

The precursor of the alkali element or elements can be any water-soluble alkali salt; preferably the precursor of the alkali element is selected from the hydroxide, nitrate and carbonate of the alkali element. Very preferably, the precursor of the alkali element(s) is the corresponding hydroxide. When the alkali element is sodium, the precursor is preferably soda (sodium hydroxide, NaOH); when the alkali element is potassium, the precursor is preferably potash (potassium hydroxide, KOH).

The quantities of the alkali element or elements introduced into the solution are selected in such a way that the total content of alkali element with respect to the total weight of the adsorbent is comprised between 1 and 60% by weight of said element, preferably comprised between 2 and 40% by weight, and very preferably comprised between 2 and 20% by weight, or even between 2 and 15% by weight or between 5 and 15% by weight.

According to step b) of the first variant of the process of preparation, an alumina support having a sodium content, expressed as $Na_2O$ equivalent, comprised between 1000 and 5000 ppm by weight with respect to the total weight of the support, is impregnated with the aqueous solution obtained at the end of step a). Impregnation of the alkali element or elements can be carried out by all the processes known to a person skilled in the art, in particular by dry impregnation, i.e. by impregnation in which the volume of the impregnation solution corresponds exactly to the volume of water uptake of the support, i.e. to the accessible pore volume of the solid. Preferably, the alkali element or elements are deposited by dry impregnation of their associated precursors on the alumina support having a sodium content, expressed as $Na_2O$ equivalent, before impregnation, comprised between 1000 and 5000 ppm by weight with respect to the total weight of the support.

The impregnation can be done in a single impregnation step. The impregnation can also advantageously be carried out in at least two cycles of impregnation. In this case, each impregnation is advantageously followed by maturation, drying and optionally calcination under the operating conditions described below for steps c), d) and e).

According to step c) of the first variant of the process of preparation, the impregnated support originating from step b) is left to mature in a water-saturated closed vessel.

Step c) of maturation of the impregnated support is carried out in a water-saturated closed vessel, preferably at a temperature comprised between 20° C. and 60° C., and for a time preferably comprised between 0.5 hour and 8 hours. Step c) of maturation is generally carried out at ambient temperature.

According to step d) of the first variant of the process of preparation, the solid originating from step c) is dried.

The drying step d) can be carried out in air, at a temperature that can be comprised between 70° C. and 250° C., preferably between 80° C. and 200° C., generally for a time preferably comprised between 1 and 24 hours.

In a variant of the first variant of the process according to the invention, the preparation of the adsorbent comprises, at the end of step d), an additional step e) comprising calcination in air in a dry or humid atmosphere. Calcination is generally carried out in air at a temperature typically comprised between 280° C. and 550° C. in a dry or humid atmosphere, preferably at a temperature between 300° C. and 500° C., and especially preferably at a temperature comprised between 350 and 450° C. The calcination is carried out at a temperature such that the formation of aluminates of alkali metals is not observed (i.e. at a relatively low temperature). Preferably, in step e), the solid originating from step d) is calcined in air with a relative humidity at 25° C. comprised between 10% and 80%, preferably between 15% and 50%.

According to a second variant, the process for the preparation of the adsorbent according to the invention can be carried out by co-granulation. Co-granulation consists of forming a mixture of powders. According to this variant, the process for the preparation of the adsorbent according to the invention comprises the following steps:

a') mixing an alumina support having a sodium content, expressed as $Na_2O$ equivalent, comprised between 1000 and 5000 ppm by weight with respect to the total weight of the support, with a powder of at least one alkali precursor, b') optionally grinding the mixture obtained at the end of step a') to a granulometry comprised between 2 and 100 µm, c') forming the mixture originating from step b') in the presence of water so as to obtain a material, d') drying the formed material originating from step c').

The alkali precursor used as powder in step a') can be one of the alkali precursors described for step a) of the process of preparation by impregnation. It is introduced in the quantities stated in step a).

The forming step c') is carried out by any technique known to a person skilled in the art, for example the methods of forming by extrusion, by pelletization, by the oil drop method (dropping) or by granulation with a rotating plate. Preferably, forming is carried out by granulation with a rotating plate.

The drying step d') is carried out under the operating conditions described for step d) of the process of preparation by impregnation.

According to a variant of the second variant of the process of preparation (co-granulation), drying can be followed by a step e') of calcination in dry or humid air under the conditions as described for step e) of the process of preparation by impregnation.

According to a third variant, the process for the preparation of the adsorbent according to the invention can be carried out by co-mixing. According to this variant, the process for the preparation of the adsorbent according to the invention comprises the following steps:

a") mixing an alumina support having a sodium content, expressed as $Na_2O$ equivalent, comprised between 1000 and 5000 ppm by weight with respect to the total weight of the support, with a solution comprising at least one alkali precursor, in order to obtain a paste, b") forming the paste obtained in step a"), c") drying the formed paste originating from step b").

The alkali precursor used in the solution in step a") can be one of the alkali precursors described for step a) of the process of preparation by impregnation. It is introduced in the quantities stated in step a).

The forming step b") is carried out by any technique known to a person skilled in the art, for example the methods of forming by extrusion, by pelletization, by the oil drop method (dropping) or by granulation with a rotating plate. Preferably, forming is carried out by extrusion.

The drying step c") is carried out under the operating conditions described for step d) of the process of preparation by impregnation.

According to a variant of the third variant of the process of preparation (co-mixing), drying can be followed by a step d") of calcination in dry or humid air under the conditions as described for step e) of the process of preparation by impregnation.

Process for the Elimination of Acidic Molecules

The invention also relates to a process for the elimination of an acidic molecule from a hydrocarbon flow containing at least one acidic molecule, in which the hydrocarbon flow is brought into contact, during an adsorption step, with an adsorbent according to the invention or one prepared by one of the processes of preparation according to the invention.

The adsorbent according to the invention is particularly suitable for capturing the COS and/or $CO_2$ contained in a liquid or gaseous flow, in particular at low temperature.

The adsorbent, for example in the form of a fixed bed arranged in a reactor, is brought into contact with the liquid or gaseous flow to be treated.

Industrially, the elimination of the acidic molecules from a flow of gaseous or liquid hydrocarbons is carried out by circulating the flow to be treated through fixed beds filled with the adsorbent. The impurity to be eliminated, here in particular the COS and/or $CO_2$, is then retained within or on the surface of the adsorbent and the flow evacuated is then purified.

Preferably, the acidic molecule to be eliminated is COS and/or $CO_2$.

The hydrocarbon flow containing COS can be a liquid or gaseous flow, preferably a liquid flow. The hydrocarbon flow treated in the process according to the invention can be a flow containing liquid or gaseous, saturated or unsaturated hydrocarbons having from 1 to 6 carbon atoms. The liquid or gaseous flow can for example be an olefinic cut originating from catalytic cracking, for example a propylene cut. Preferably, the hydrocarbon flow is a flow of liquid propylene.

The hydrocarbon flow to be treated according to the invention contains COS in variable proportions. For example, the hydrocarbon flow to be treated, in particular a flow of liquid propylene, contains between 10 and 200 ppm by weight of COS.

The hydrocarbon flow containing $CO_2$ can be a liquid or gaseous flow, preferably a gaseous flow. The hydrocarbon flow treated in the process according to the invention can be a flow containing liquid or gaseous, saturated or unsaturated hydrocarbons having from 1 to 6 carbon atoms. The liquid or gaseous flow can for example be an olefinic cut originating from catalytic cracking, for example an ethylene cut. It can also originate from a process for the dehydration of alcohol, in particular for the dehydration of ethanol or butanol. Preferably, the hydrocarbon flow is a flow of gaseous ethylene or of liquid butene.

The $CO_2$ content is generally comprised between 10 and 500 ppm-molar of $CO_2$ in the hydrocarbon flow.

If present, $H_2S$ will be at least partially adsorbed by the adsorbent according to the invention.

Bringing the hydrocarbon flow into contact with the adsorbent according to the invention can be carried out at a temperature generally comprised between −50 and 100° C., preferably between 0 and 70° C., and very preferably between 20 and 50° C., and at an absolute pressure for example comprised between 0.01 MPa and 20 MPa (0.1 and 200 bar), preferably between 0.05 MPa and 10 MPa (0.5 and 100 bar) and very preferably between 0.1 MPa and 5 MPa (1 and 50 bar).

Advantageously, when the hydrocarbon flow is brought into contact with the adsorbent, the HSV (hourly space velocity, or the volume of effluent per volume of adsorbent and per hour) implemented in the process of elimination according to the invention is comprised between 50 and 50,000 $h^{-1}$.

The hydrocarbon flow can optionally contain water. Preferably, if the hydrocarbon flow contains water, it is dried beforehand by any process known to a person skilled in the art. Preferably, the hydrocarbon flow is dried by passage over a bed of zeolite, for example of the LTA type exchanged with sodium or potassium.

Contact with the adsorbent advantageously makes it possible to capture the COS and/or $CO_2$ in the flow to be treated, and to obtain a flow having a content of COS and/or $CO_2$ that is reduced with respect to the content in the initial flow, or even to completely eliminate the COS and/or $CO_2$.

Advantageously, the decrease in total content of COS and/or $CO_2$ between the hydrocarbon flow before treatment and the hydrocarbon flow obtained after treatment with the adsorbent according to the invention can represent at least 90%, preferably at least 95%, and more preferably at least 99%.

According to a variant, a step of regeneration of the adsorbent is carried out once the adsorbent is at least partially saturated with acidic molecules, in particular with COS and/or $CO_2$.

The adsorbent, at least partially saturated with acidic molecules, in particular with COS and/or $CO_2$, is regenerated by passage of a gas or a liquid. The gas can be air, nitrogen, gaseous hydrocarbons, dry or humid. The liquid can be a hydrocarbon.

Bringing the regeneration gas or liquid into contact with the adsorbent according to the invention can be carried out at a temperature generally comprised between 20 and 500° C., preferably between 50 and 350° C., and very preferably between 100 and 300° C., and at an absolute pressure for example comprised between 0.01 MPa and 20 MPa (0.1 and 200 bar), preferably between 0.05 MPa and 10 MPa (0.5 and 100 bar), and very preferably between 0.1 MPa and 5 MPa (1 and 50 bar).

Advantageously, when the regeneration gas or liquid is brought into contact with the adsorbent, the HSV (hourly space velocity, or volume of effluent per volume of adsorbent and per hour) implemented in the regeneration phase according to the invention is comprised between 50 and 50,000 $h^{-1}$. This regeneration step is preferably carried out in countercurrent to the circulation of the hydrocarbon flow during the adsorption step.

The regeneration step can be implemented once the adsorbent is completely saturated or partially saturated. Preferably, the regeneration step is implemented as soon as acidic molecules are detected in the outgoing effluent.

The regeneration step can be implemented successively or in parallel with the adsorption step if the process provides two beds of adsorbents in parallel. Preferably, the adsorbent is arranged in two beds in parallel so that the regeneration of one adsorbent is implemented during the adsorption step of another adsorbent.

The examples presented below illustrate the operation and the advantages of the present invention.

EXAMPLE A

Preparation of an Adsorbent $A_I$ According to the Invention

Adsorbent $A_I$ was prepared by dry impregnation of a support of the flash alumina type prepared by granulation with a solution of NaOH. Dry impregnation consists of bringing the support into contact with a volume of impregnation solution that corresponds exactly to its available pore volume.

The support selected has a pore volume of 0.5 mL/g, a specific surface area of 341 $m^2/g$ and a sodium content, expressed as $Na_2O$ equivalent, before impregnation of 2610 ppm by weight. The specific surface area is determined in the present invention by the B.E.T method according to standard ASTM D3663, a method that is described in the same work Rouquerol F.; Rouquerol J.; Singh K. "Adsorption by Powders & Porous Solids: Principle, methodology and applications", Academic Press, 1999. The total pore volume is measured by mercury porosimetry according to standard ASTM D4284 with a wetting angle of 140°, as described in the work cited above, for example by means of the model Autopore III™ trade mark Micromeritics™. The $Na_2O$ content before and after impregnation is measured by atomic absorption spectroscopy by the process described in the work by J. Lynch "Physicochemical analysis of industrial catalysts-Practical manual for characterization", Editions Technip, 2001.

In order to obtain an adsorbent $A_1$ after impregnation at 6.5% by weight of sodium, expressed as $Na_2O$ equivalent, starting from 10 g of solution, the procedure is as follows:
a) preparation of 50 mL of solution by dissolving 8.84 g of NaOH in 50 g of water;
b) dropwise impregnation with 5 mL of the soda solution prepared in step a), which is poured using a burette onto the alumina support placed in a rotating bowl granulator,
c) maturation of the impregnated support in a water-saturated closed vessel at 20° C., for 3 hours,
d) drying the solid at 90° C. for 3 hours,
e) calcination of the solid under air at 350° C. for 1 hour.

EXAMPLE B

Preparation of an Adsorbent $A_2$ According to the Invention

Adsorbent $A_2$ was prepared by dry impregnation of the same support as in example A with a solution of KOH.

In order to obtain an adsorbent $A_2$ after impregnation at 6.5% by weight of potassium, expressed as $K_2O$ equivalent, starting from 10 g of solution, the procedure is as follows:
a) preparation of 50 mL of solution by dissolving 11.75 g of KOH in 50 g of water;
b) dropwise impregnation of 5 mL of the potash solution prepared in step a), which is poured using a burette onto the alumina support placed in a rotating bowl granulator,
c) maturation of the impregnated support in a water-saturated closed vessel at 20° C., for 3 hours,
d) drying the solid at 90° C. for 3 hours,
e) calcination of the solid under air at 350° C. for 1 hour.

EXAMPLE C

Preparation of an Adsorbent $A_3$ According to the Invention

Adsorbent $A_3$ was prepared by co-granulation of the same support as in example A with potassium carbonate.

In order to obtain an adsorbent $A_3$ at 6.5% by weight of potassium, expressed as $K_2O$ equivalent, starting from powders of alumina and potassium carbonate, the procedure is as follows:
a) intimate mixing of 9.44 g of the support and 4.68 g of $K_2CO_3$,
b) grinding the mixture to between 50 and 100 µm,
c) granulation in a rotary plate granulator in the presence of sprayed water,
d) drying the co-granulated product at 90° C. for 3 hours,
e) calcination of the co-granulated product under air at 350° C. for 1 hour.

EXAMPLE D

Preparation of an Adsorbent $A_4$ (Comparative)

Adsorbent $A_4$ was prepared by dry impregnation of a support of the flash alumina type prepared by granulation with a solution of NaOH.

The support selected has a pore volume of 0.6 mL/g, a specific surface area of 313 m$^2$/g and a sodium content, expressed as $Na_2O$ equivalent, before impregnation of 760 ppm by weight.

In order to obtain an adsorbent $A_4$ after impregnation at 6.5% by weight of sodium, expressed as $Na_2O$ equivalent, starting from 10 g of solution, the procedure is as follows:
a) preparation of 50 mL of solution by dissolving 7.52 g of NaOH in 50 g of water;
b) dropwise impregnation of 6 mL of the soda solution prepared in step a), which is poured using a burette onto the alumina support placed in a rotating bowl granulator,
c) maturation of the impregnated support in a water-saturated closed vessel at 20° C., for 3 hours,
d) drying the solid at 90° C. for 3 hours,
e) calcination of the solid under air at 350° C. for 1 hour.

EXAMPLE E

Preparation of an Adsorbent $A_5$ (Comparative)

Adsorbent $A_5$ was prepared by dry impregnation of a support of the alumina gel type prepared by mixing-extrusion with a solution of NaOH.

The support selected has a pore volume of 0.7 mL/g, a specific surface area of 282 m$^2$/g and a sodium content, expressed as $Na_2O$ equivalent, before impregnation of 570 ppm by weight.

In order to obtain an adsorbent $A_5$ after impregnation at 6.5% by weight of sodium, expressed as $Na_2O$ equivalent, starting from 10 g of solution, the procedure is as follows:
a) preparation of 50 mL of solution by dissolving 6.44 g of NaOH in 50 g of water;
b) dropwise impregnation of 7 mL of the soda solution prepared in step a), which is poured using a burette onto the alumina support placed in a rotating bowl granulator,
c) maturation of the impregnated support in a water-saturated closed vessel at 20° C., for 3 hours,
d) drying the solid at 90° C. for 3 hours,
e) calcination of the solid under air at 350° C. for 1 hour.

EXAMPLE F

Preparation of an Adsorbent $A_6$ (Comparative)

Adsorbent $A_6$ was prepared by dry impregnation of a support of the flash alumina type prepared by granulation with a solution of NaOH.

The support selected has a pore volume of 0.35 mL/g, a specific surface area of 267 m$^2$/g and a sodium content, expressed as $Na_2O$ equivalent, before impregnation of 6340 ppm by weight.

In order to obtain an adsorbent $A_6$ after impregnation at 6.5% by weight of sodium, expressed as $Na_2O$ equivalent, starting from 10 g of solution, the procedure is as follows:
a) preparation of 50 mL of solution by dissolving 12.79 g of NaOH in 50 g of water;
b) dropwise impregnation of 3.5 mL of the soda solution prepared in step a), which is poured using a burette onto the alumina support placed in a rotating bowl granulator,
c) maturation of the impregnated support in a water-saturated closed vessel at 20° C., for 3 hours,
d) drying the solid at 90° C. for 3 hours,
e) calcination of the solid under air at 350° C. for 1 hour.

EXAMPLE G

Tests of the COS Adsorption Capacities of the Various Adsorbents $A_1$, $A_2$, $A_3$, $A_4$, $A_5$ and $A_6$ The COS adsorption performance of the adsorbents thus prepared is tested in a fixed-bed reactor with a volume of 1.5 cm³.

First, the solids are activated at 290° C. under 10 NL/h of nitrogen for 12 hours. Then a liquid flow of propylene containing 50 ppm by weight of COS is passed through the bed of adsorbents at a flow rate of 50 g/h, at a temperature of 50° C. and a pressure of 2 MPa. The COS concentration is measured at the reactor outlet by means of a chromatogram equipped with a sulphur-specific detector (PFPD). These operating conditions are applied to each sample of adsorbent until the latter is saturated. The adsorbent is considered to be saturated when the COS concentrations at the reactor outlet become equal to those of the feedstock. The adsorbent is then heated at 290° C. under a nitrogen flow (5 NL/h) in order to desorb the COS adsorbed in the preceding step for about 10 hours. Once regenerated, the adsorbent is again exposed to the flow of liquid propylene containing 50 ppm by weight of COS under the same conditions as described above. For each adsorbent, four cycles of adsorption/desorption are carried out successively.

For each cycle, the quantity of COS that is chemisorbed on each adsorbent can be evaluated by carrying out a material balance on the COS between the reactor inlet and the reactor outlet over the entire test duration. The relative capacities at COS saturation ($q_{sat}$ in g of COS per 100 g of adsorbent) of the various adsorbents are shown in Table 1.

TABLE 1

| Adsorbent | Na content (ppmw Na₂O) of the support before introducing the alkali element | $q_{sat}$ (g/100 g of adsorbent) | | | |
|---|---|---|---|---|---|
| | | Cycle 1 | Cycle 2 | Cycle 3 | Cycle 4 |
| $A_1$ | 2610 | 2.05 | 1.72 | 1.70 | 1.71 |
| $A_2$ | 2610 | 2.58 | 2.15 | 2.18 | 2.17 |
| $A_3$ | 2610 | 2.27 | 1.78 | 1.86 | 1.81 |
| $A_4$ | 760 | 2.30 | 1.46 | 1.15 | 0.97 |
| $A_5$ | 570 | 2.62 | 1.39 | 0.94 | 0.78 |
| $A_6$ | 6340 | 1.34 | 0.77 | 0.73 | 0.76 |

These examples show that in the second cycle, compared to the first cycle, the adsorbents prepared all lose a small quantity of COS adsorption capacity, which is attributed to irreversible adsorption of some of the COS on the strongest adsorption sites. Thereafter, the COS adsorption performance only stabilizes for the adsorbents prepared according to the invention. For the two comparative adsorbents prepared from supports insufficiently stabilized with sodium, the adsorption capacities continue to decrease during the cycles of adsorption/regeneration after the 2nd cycle. For the comparative adsorbent having a sodium content that is too high (greater than 5000 ppm by weight), the performance is stable beyond the second cycle but is very clearly poorer. This is attributed to poorer dispersion of the active phase on the surface of the solid, leading to poorer accessibility of the adsorption sites.

EXAMPLE H

Tests of the $CO_2$ Adsorption Capacities of the Various Adsorbents $A_1$, $A_2$, $A_3$, $A_4$, $A_5$ and $A_6$ The $CO_2$ adsorption performance of the adsorbents thus prepared is tested in a fixed-bed reactor with a volume of 1.5 cm³.

First, the solids are activated at 290° C. under 10 NL/h of nitrogen for 12 hours. Then a gaseous flow of ethylene containing 200 ppm-molar of $CO_2$ is passed through the bed of adsorbents at a flow rate of 5 NL/h, at a temperature of 50° C. and a pressure of 0.1 MPa. The concentration of $CO_2$ is measured at the reactor outlet by means of a chromatogram equipped with a cathetometer. These operating conditions are applied to each sample of adsorbent until the latter is saturated. The adsorbent is considered to be saturated when the concentrations of $CO_2$ at the reactor outlet become equal to that of the feedstock. The adsorbent is then heated at 290° C. under a nitrogen flow (5 NL/h) in order to desorb the $CO_2$ adsorbed in the preceding step for about 10 hours. Once regenerated, the adsorbent is again exposed to the flow of gaseous ethylene containing 200 ppm-molar of $CO_2$ under the same conditions as described above. For each adsorbent, four cycles of adsorption/desorption are carried out successively.

For each cycle, the quantity of $CO_2$ that is chemisorbed on each adsorbent can be evaluated by carrying out a material balance on the $CO_2$ between the reactor inlet and the reactor outlet over the entire test duration. The relative capacities at saturation with $CO_2$ ($q_{sat}$ in g of $CO_2$ per 100 g of adsorbent) of the various samples in weights captured are shown in Table 2.

TABLE 2

| Adsorbent | Na content (ppmw Na₂O) of the support before introducing the alkali element | $q_{sat}$ | | | |
|---|---|---|---|---|---|
| | | Cycle 1 | Cycle 2 | Cycle 3 | Cycle 4 |
| $A_1$ | 2610 | 1.88 | 1.85 | 1.82 | 1.87 |
| $A_2$ | 2610 | 2.44 | 2.37 | 2.42 | 2.40 |
| $A_3$ | 2610 | 2.21 | 2.09 | 2.18 | 2.13 |
| $A_4$ | 760 | 2.26 | 1.97 | 1.86 | 1.74 |
| $A_5$ | 570 | 2.46 | 2.35 | 1.97 | 1.80 |
| $A_6$ | 6340 | 1.60 | 1.51 | 1.45 | 1.49 |

These examples show that the adsorbents according to the invention are those that have the highest stabilized performance. Adsorbents $A_4$ and $A_5$, which do not have enough sodium before impregnation, lose capacity during the cycles. Adsorbent $A_6$, in which the sodium content is too high (greater than 5000 ppm by weight), has stable, but definitely poorer, performance. This is attributed to poorer dispersion of the active phase on the surface of the solid, leading to poorer accessibility of the adsorption sites.

The invention claimed is:
1. An adsorbent comprising an alumina support and at least one alkali element, said adsorbent being obtained by the introduction of at least one alkali element, identical to or different from sodium, onto an alumina support the sodium content of which, expressed as Na₂O equivalent, before the introduction of the alkali element or elements, is comprised between 1500 and 3500 ppm by weight with respect to the total weight of the support.

2. The adsorbent according to claim 1, in which the alkali element is sodium or potassium.

3. The adsorbent according to claim 1, in which the content of alkali element with respect to the total weight of the adsorbent is 1 to 60% by weight of said element.

4. The adsorbent according to claim 1, in which the sodium content, expressed as $Na_2O$ equivalent, in the alumina support before the introduction of the alkali element or elements is 2000 to 3000 ppm by weight with respect to the total weight of the support.

5. The adsorbent according to claim 1, in which the alumina support before the introduction of the alkali element or elements has a total pore volume of 0.3 to 1 $cm^3.g^{-1}$ and a specific surface area of 50 to 450 $m^2.g^{-1}$.

6. The adsorbent according to claim 1, comprising potassium and the alumina support having a sodium content, expressed as $Na_2O$ equivalent, before the introduction of the potassium, of 1500 to 3500 ppm by weight with respect to the total weight of the support.

\* \* \* \* \*